US007973015B2

(12) United States Patent
van Ommen et al.

(10) Patent No.: US 7,973,015 B2
(45) Date of Patent: Jul. 5, 2011

(54) INDUCTION OF EXON SKIPPING IN EUKARYOTIC CELLS

(75) Inventors: Garrit-Jan B. van Ommen, Amsterdam (NL); Judith C. T. van Deutekom, Dordrecht (NL); Johannes T. den Dunnen, Rotterdam (NL)

(73) Assignee: Academisch Ziekenhuis Leiden, Leiden (NL)

( * ) Notice: Subject to any disclaimer, the term of this patent is extended or adjusted under 35 U.S.C. 154(b) by 6 days.

(21) Appl. No.: 10/395,031

(22) Filed: Mar. 21, 2003

(65) Prior Publication Data
US 2003/0235845 A1 Dec. 25, 2003

Related U.S. Application Data

(63) Continuation of application No. PCT/NL01/00697, filed on Sep. 21, 2001.

(30) Foreign Application Priority Data

Sep. 21, 2000 (EP) .................................... 00203283

(51) Int. Cl.
*A61K 48/00* (2006.01)
*C07H 21/04* (2006.01)
(52) U.S. Cl. ......................................... 514/44; 536/24.5
(58) Field of Classification Search .................. None
See application file for complete search history.

(56) References Cited

U.S. PATENT DOCUMENTS

| | | | |
|---|---|---|---|
| 5,593,974 | A | 1/1997 | Rosenberg et al. |
| 5,968,909 | A | 10/1999 | Agrawal et al. |
| 6,172,216 | B1 | 1/2001 | Bennett et al. |
| 6,653,466 | B2 | 11/2003 | Matsuo |
| 6,653,467 | B1 | 11/2003 | Matsuo et al. |
| 6,727,355 | B2 | 4/2004 | Matsuo et al. |
| 7,534,879 | B2 | 5/2009 | van Deutekom |
| 2001/0056077 | A1 | 12/2001 | Matsuo |
| 2002/0049173 | A1 | 4/2002 | Bennett et al. |
| 2002/0055481 | A1 | 5/2002 | Matsuo et al. |

FOREIGN PATENT DOCUMENTS

| | | |
|---|---|---|
| CA | 2319149 A1 | 9/2000 |
| EP | 0850300 | 7/1998 |
| EP | 1 054 058 A1 | 11/2000 |
| EP | 1 133 993 A1 | 9/2001 |
| EP | 1160318 | 12/2001 |
| EP | 1 191 097 A1 | 3/2002 |
| WO | WO-9301286 | 1/1993 |
| WO | WO-9712899 | 4/1997 |
| WO | WO 97/30067 | 8/1997 |
| WO | WO 02/24906 A1 | 3/2002 |
| WO | WO 2004/083432 A1 | 9/2004 |

OTHER PUBLICATIONS

Dunckley et al. Modification of splicing in the dystrophin gene in cultured Mdx muscle cells by antisense oligoribonucleotides. Hum Mol Genet. Jul. 1998;7(7):1083-90.*
Pramono et al. Induction of exon skipping of the dystrophin transcript in lymphoblastoid cells by transfecting an antisense oligodeoxynucleotide complementary to an exon recognition sequence. Biochem Biophys Res Commun. Sep. 13, 1996;226(2):445-9.*
Bremmer-Bout et al. Targeted exon skipping in transgenic hDMD mice: A model for direct preclinical screening of human-specific antisense oligonucleotides. Mol Ther. Aug. 2004;10(2):232-40.*
Errington et al. Target selection for antisense oligonucleotide induced exon skipping in the dystrophin gene. J Gene Med. Jun. 2003;5(6):518-27.*
van Deutekom et al. Antisense-induced exon skipping restores dystrophin expression in DMD patient derived muscle cells. Hum Mol Genet. Jul. 15, 2001;10(15):1547-54.*
Mann et al. Antisense-induced exon skipping and synthesis of dystrophin in the mdx mouse. Proc Natl Acad Sci U S A. Jan. 2, 2001;98(1):42-7.*
Mann et al. Improved antisense oligonucleotide induced exon skipping in the mdx mouse model of muscular dystrophy. J Gene Med. Nov.-Dec. 2002;4(6):644-54.*
van Deutekom et al. (2001) 10:1547-1554.*
Matsuo et al. Brain Devl. (1996) 18:167-172.*
Brown et al. "Structure and mutation of the dystrophin gene" in Dystrophin: Gene, protein and cell biology, (Brown and Lucy, eds.), Cambridge University Press, Cambridge, 1997,pp. 1-26.*
Roberts et al. (1994) Hum. Mut. 4:1-11.*
Nishino et al. (1994) J. Clin. Invest. 94:1037-1042.*
Sertic et al. (1997) Coll. Antropol. 1:151-156.*
Crooke (In Basic Principles of Antisense Therapeutics, Springer-Verlag, Eds, New York, 1998, pp. 1-50).*
Gryzanov (Biochim. Biophys. Acta 1489:131-140, 1999).*
Agrawal et al (Mol. Med. Today 6:72-81, 2000).*
Opalinska et al (Nature Reviews Drug Discovery, 2002, vol. 1, pp. 503-514).*
Scanlon (Curr. Pharm. Biotech. 5:415-420, 2004).*
Verreault et al (Curr. Gene Ther. 6: 505-533, 2006).*
Van Vliet et al (BMC Med. Gen. 9:105, 2008).*
International Search Report, International Application No. PCT/NL01/00697, dated Dec. 21, 2001 (2 pages).
International Preliminary Examination Report, International Application No. PCT/NL01/00697, dated Aug. 1, 2002 (2 pages).

(Continued)

*Primary Examiner* — Richard Schnizer
(74) *Attorney, Agent, or Firm* — Edwards Angell Palmer & Dodge LLP; Elizabeth Spar; Kathleen Williams

(57) ABSTRACT

The present invention provides a method for at least in part decreasing the production of an aberrant protein in a cell, the cell comprising pre-mRNA comprising exons coding for the protein, by inducing so-called exon skipping in the cell. Exon-skipping results in mature MRNA that does not contain the skipped exon, which leads to an altered product of the exon codes for amino acids. Exon skipping is performed by providing a cell with an agent capable of specifically inhibiting an exon inclusion signal, for instance, an exon recognition sequence, of the exon. The exon inclusion signal can be interfered with by a nucleic acid comprising complementarity to a part of the exon. The nucleic acid, which is also herewith provided, can be used for the preparation of a medicament, for instance, for the treatment of an inherited disease.

4 Claims, 9 Drawing Sheets

OTHER PUBLICATIONS

Aartsma-Rus et al., "Functional Analysis of 114 Exon-Internal AONs for Targeted DMD Exon Skipping: Indication for Steric Hindrance of SR Protein Binding Sites," Oligonucleotides, 2005, pp. 284-297, vol. 15.

Dunckley et al., Modulation of Splicing in the DMD Gene by Antisense Oligoribonucleotides, Nucleosides & Nucleotides, 1997, pp. 1665-1668, vol. 16, No. 7-9.

Sherratt et al., Exon Skipping and Translation in Patients with Frameshift Deletions in the Dystrophin Gene, Am. J. Hum. Genet., 1993, pp. 1007-1015, vol. 53.

Tanaka et al., Polypurine Sequences within a Downstream Exon Function as a Splicing Enhanced, Molecular and Cellular Biology, Feb. 1994, pp. 1347-1354, vol. 14, No. 2.

Letter from Katholieke Universiteit Leuven to Dr. N. Goemans, Child Neurology, UZ Leuven dated Jan. 22, 2008 regarding A Phase I/II, open label, escalating dose, pilot study to assess the effect, safety, tolerability and pharmacokinetics of multiple subcutaneous doses of PRO051 in patients with Duchenne muscular dystrophy. PRO051-02 (translation provided).

Letter from Prosensa Therapeutics B.V. to Federal Agency for Medicines and Health Products dated Jan. 9, 2008 regarding A phase I/II, open label, escalating dose, pilot study to assess the effect, safety, tolerability and pharmacokinetics of multiple subcutaneous doses of PRO051 in patients with Duchenne muscular dystrophy.

Hope for muscular dystrophy drug, The Daily Telegraph, Dec. 28, 2007.

New Clinical Trial Results Show How Personalized Medicine Will Alter Treatment of Genetic Disorders, Medical News Today, Dec. 29, 2007 <http://www.medicalnewstoday.com/articles/92777.php>.

Hansen, Product Development—Addition by subtraction, BioCentury, The Bernstein Report on BioBusiness, Jan. 7, 2008, p. A28 of 38.

LUMC and Prosensa report positive results of DMD study, Pharmaceutical Business Review Online, dated Dec. 28, 2007, <http://www.pharmaceutical-business-review.com/article_news_print.asp?guid=8462FD44-F35D-4EOB-BC>.

TREAT-NMD Neuromuscular Network, Jan. 11, 2008.

Bionity.Com NEWS-Center, Leiden University Medical Center and Prosensa B.V. Announce First Successful Clinical Study with RNA-based Therapeutic PRO051, dated Jan. 3, 2008, <http://www.bionity.com/news/e/76185>.

Biopharmaceutiques, Merging Pharma & Biotech, Edition 48, Jan. 10, 2008, <http://www.biopharmaceutiques.com/en/num>, visited Jan. 11, 2008.

Leiden University Medical Center and Prosensa B.V. Announce New England Journal of Medicine Publication of First Successful Clinical Study with RNA-based Therapeutic PRO051 in Duchenne Muscular Dystrophy, Dec. 27, 2007.

Grady, Early drug test shows promise in treating muscular dystrophy, International Herald Tribune, Jan. 3, 2008, Health & Science, p. 9.

Grady, Promising Dystrophy Drug Clears Early Test, The New York Times, Dec. 27, 2007.

Hoffman, Skipping toward Personalized Molecular Medicine, N. Engl. J. Med., Dec. 27, 2007, pp. 2719-2722, vol. 357, No. 26.

Van Deutekom et al., Local Dystrophin Restoration with Antisense Oligonucleotide PRO051, N. Engl. J. Med., Dec. 27, 2007, pp. 2677-2686.

Wilton et al., Specific removal of the nonsense mutation from the mdx dystrophin mRNA using antisense oligonuleotides, Neuromuscular Disorders, 1999, pp. 330-338, vol. 9.

Aartsma-Rus et al., Exploring the Frontiers of Therapeutic Exon Skipping for Duchenne Muscular Dystrophy by Double Targeting within One or Multiple Exons, Molecular Therapy, 2006, pp. 1-7.

Muntoni et al., 149th ENMC International Workshop and 1st TREAT-NMD Workshop on: "Planning Phase I/II Clinical trials using Systemically Delivered Antisense Oligonucleotides in Duchenne Muscular Dystrophy," Neuromuscular Disorders, 2008, pp. 268-275, vol. 18.

Yokota et al., Efficacy of Systemic Morpholino Exon-Skipping in Duchenne Dystrophy Dogs, Ann Neurol., 2009, pp. 667-676, vol. 65.

Dickson et al., Screening for antisense modulation of dystrophin pre-mRNA splicing, Neuromuscul. Disord., 2002, S67-70, Suppl. 1.

De Angelis et al., Chimeric snRNA molecules carrying antisense sequences against the splice junctions of exon 51 of the dystrophin pre-mRNA induce exon skipping and restoration of a dystrophin synthesis in delta 48-50 DMD cells, PNAS, Jul. 9, 2002, pp. 9456-9461, vol. 99, No. 14.

Lu et al., Massive Idiosyncratic Exon Skipping Corrects the Nonsense Mutation in Dystrophic Mouse Muscle and Produces Functional Revertant Fibers by Clonal Expansion, The Journal of Cell Biology, Mar. 6, 2000, pp. 985-995, vol. 148, No. 5.

Suter et al., Double-target antisense U7 snRNAs promote efficient skipping of an aberrant exon in three human B-thalassemic mutations, Human Molecular Genetics, 1999, pp. 2415-2423, vol. 8, No. 13.

Abbs et al., A convenient multiplex PCR system for the detection of dystrophin gene deletions: a comparative analysis with cDNA hybridisation shows mistypings by both methods, J. Med. Genet, 1991, pp. 304-311, vol. 28.

Dirksen et al., Mapping the SF2/ASF Binding Sites in the Bovine Growth Hormone Exonic Splicing Enhancer, The Journal of Biological Chemistry, Sep. 15, 2000, pp. 29170-29177, vol. 275, No. 37.

Hussey et al., Analysis of five Duchenne muscular dystrophy exons and gender determination using conventional duplex polymerase chain reaction on single cells, Molecular Human Reproduction, 1999, pp. 1089-1094, vol. 5, No. 11.

Karras et al., Deletion of Individual Exons and Induction of Soluble Murine Interleukin-5 Receptor-alpha Chain Expression through Antisense Oligonucleotide-Mediated Redirection of Pre-mRNA Splicing, Molecular Pharmacology, 2000, pp. 380-387, vol. 58.

Liu et al., Identification of functional exonic splicing enhancer motifs recognized by individual SR proteins, Genes & Development, 1998, pp. 1998-2012, vol. 12.

Monaco et al., An Explanation for the Phenotypic Differences between Patients Bearing Partial Deletions of the DMD Locus, Genomics, 1988, pp. 90-95, vol. 2.

Shiga et al., Disruption of the Splicing Enhancer Sequence within Exon 27 of the Dystrophin Gene by a Nonsense Mutation Induces Partial Skipping of the Exon and Is Responsible for Becker Muscular Dystrophy, J. Clin. Invest., Nov. 1997, pp. 2204-2210, vol. 100, No. 9.

Simoes-Wust et al., bcl-xL Antisense Treatment Induces Apoptosis in Breast Carcinoma Cells, Int. J. Cancer, 2000, pp. 582-590, vol. 87.

Takeshima et al., Modulation of In Vitro Splicing of the Upstream Intron by Modifying an Intra-Exon Sequence Which Is Deleted from the Dystrophin Gene in Dystrophin Kobe, J. Clin. Invest., Feb. 1995, pp. 515-520, vol. 95.

Watakabe et al., The role of exon sequences in splice site selection, Genes & Development, 1993, pp. 407-418, vol. 7.

U.S. Appl. No. 11/919,248, filed Feb. 28, 2008, van Deutekom et al., Modulation of Exon Recognition in pre-mRNA by Interfering with the Binding of SR Proteins and by Interfering with Secondary RNA Structure.

U.S. Appl. No. 12/383,897, filed Mar. 30, 2009, van Ommen et al., Induction of Exon Skipping in Eukaryotic Cells.

Aartsma-Rus et al: "Targeted exon skipping as a potential gene correction therapy for Duchenne muscular dystrophy." Neuromuscular Disorders, 2002, pp. S71-S77.

Arzumanov et al: "Inhibition of HIV-1 Tat-dependent trans activation by steric block chimeric 2'-O-methyl/LNA oligoribonucleotides." Biochemistry, 2001, vol. 40, pp. 14645-14654.

International Search Report, International Application No. PCT/NL2004/000196, Oct. 28, 2004 (8 pages).

Kurrek et al: "Design of antisense oligonucleotides stabilized by locked nucleic acids." Nucleic Acids Research, 2002, vol. 30, No. 9, pp. 1911-1918.

Rando: "Oligonucleotide-mediated gene therapy for muscular dystrophies." Neuromuscular Disorders, 2002, vol. 12, pp. S55-S60.

Shapiro and Senapathy: "RNA splice junctions of different classes of eukaryotes: sequence statistics and functional implications in gene expression." Nucleic Acids Research, 1987, vol. 15, No. 17, pp. 7155-7174.

Thanh et al: "Characterization of revertant muscle fibers in Duchenne muscular dystrophy, using exon-specific monoclonal antibodies against dystrophin." Am. J. Hum. Genet., 1995, vol. 56, pp. 725-731.

Notice of Opposition filed against EP 1 619 249 B, dated Jun. 23, 2009.
Office Action for U.S. Appl. No. 11/233,507, dated Jun. 15, 2007.
Office Action for U.S. Appl. No. 11/233,507, dated Mar. 19, 2008.
Office Action for U.S. Appl. No. 11/233,507, dated Nov. 12, 2008.
Office Action for U.S. Appl. No. 11/233,507, dated May 29, 2009.
Office Action for U.S. Appl. No. 11/233,495, dated Dec. 1, 2008.
Office Action for U.S. Appl. No. 11/233,495, dated Jun. 25, 2009.
Office Action for U.S. Appl. No. 11/982,285, dated May 4, 2009.
Office Action for U.S. Appl. No. 11/982,285, dated Sep. 18, 2009.
U.S. Appl. No. 11/233,507, filed Sep. 21, 2005, van Deutekom et al., Modulation of Exon Recognition in pre-mRNA by Interfering with the Secondary RNA Structure.
U.S. Appl. No. 11/233,495, filed Sep. 21, 2005, van Ommen et al., Modulation of Exon Recognition in pre-mRNA by Interfering with the Secondary RNA Structure.
U.S. Appl. No. 11/919,248, filed Feb. 28, 2008, van Deutekom et al., Modulation of Exon Recognition in pre-mRNA by Interfering with the Binding of SR Proteins and by Interfering With Secondary RNA Structure.
U.S. Appl. No. 11/982,285, filed Oct. 31, 2007, van Ommen et al., Induction of Exon Skipping in Eukaryotic Cells.
U.S. Appl. No. 12/383,897, filed Mar. 30, 2009, van Ommen et al., Induction of Exon Skipping in Eukaryotic Cells.
Erba et al., "Structure, chromosome location, and expression of the human gamma—actin gene: different evolution, location, and express of the cytoskeletal beta- and gamma- actin genes." Mol. Cell. Biology, 8(4): 1775-89, 1988.
Munroe, "Antisense RNA inhibits splicing of pre-mRNA in vitro." EMBO J., 7(8): 2523-2532, 1988.
Feener et al., "Alternative splicing of human dystrophin mRNA generates isoforms at the carboxy terminus." Nature, 338 (6215): 509-511, 1989.
Roberts et al., "Direct diagnosis of carriers of Duchenne and Becker muscular dystrophy by amplification of lymphocyte RNA." Lancet, 336 (8730-8731): 1523-6, 1990.
Roberts et al., "Direct detection of dystrophin gene rearrangements by analysis of dystrophin mRNA in peripheral blood lymphocytes." Am. J. Hum. Genet., 49(2): 298-310, 1991.
Barabino et al., "Antisense probes targeted to an internal domain in US snRNP specifically inhibit the second step of pre-mRNA splicing." Nucleic Acids Res. 20(17): 4457-4464, 1992.
Matsuo et al., "Partial deletion of a dystrophin gene leads to exon skipping and to loss of an intra-exon hairpin structure from the predicted mRNA precursor." Biochem. Biophys. Res. Commun. 182(2): 495-500, 1992.
Roberts et al., "Exon structure of the human dystrophin gene." Genomics, 16(2): 536-538, 1993.
Laptev et al., "Specific inhibition of expression of a human collagen gene (COL1A1) with modified antisense oligonucleotides. The most effective target sites are clustered in double-stranded regions of the predicted secondary structure for the mRNA." Biochemistry, 33(36): 11099-11039, 1994.
Roberts et al., "Search for the 1 in 2,400,000: a review of dystrophin gene point mutations." Hum. Mutat. 4(1): 1-11, 1994.
Nishio et al., "Identification of a novel first exon in the human dystrophin gene and of a new promoter located more than 500 kb upstream of the nearest known promoter." Journal of Clinical Investigation, 94(3): 1037-42, 1994.
Matsuo, "Duchenne/Becker muscular dystrophy: from molecular diagnosis to gene therapy." Brain Dev. May-Jun; 18(3): 167-72, 1996.
Pramono et al., "Induction of exon skipping of the dystrophin transcript in lymphoblastoid cells by transfecting an antisense oligodeoxynucleotide complementary to an exon recognition sequence." Biochem. Biophys. Res. Commun., Sep. 13; 226(2): 445-9, 1996.
Brown et al., "Structure and mutation of the dystrophin gene" in Dystrophin: Gene, protein and cell biology, (Brown and Lucy, eds). Cambridge University Press, Cambridge, 1997, pp1-16.
Coulter et al., "Identification of a new class of exonic splicing enhancers by in vivo selection." Mol. Cell. Biol., 17(4): 2143-50, 1997.
Sertic et al., "Deletion screening of the Duchenne/Becker muscular dystrophy gene in Croatian population." Coll. Antropol., Jun: 21(1): 151-6, 1997.
Crooke, Basic Principles of Antisense Therapeutics, Springer-Verlag Eds, New York, pp. 1-50, 1998.
Gryaznov, "Oligonucleotide N3'—P5' phosphoramidates as potential therapeutic agents." Biochim. Biophys. Acta. Dec. 10; 1489(1): 131-140, 1999.
Ginjaar et al., "Dystrophin nonsense mutation induces different levels of exon 29 skipping and leads to variable phenotypes within one BMD family." European J. Of Human Genetics, 8, 793-796, 2000.
Genes VII, Jan. 2000, Benjamin Lewin, Chapter 22, Nuclear Splicing, pp. 704-705.
Agrawal and Kandimall, "Antisense therapeutics: is it as simple as complementary base recognition?" Mol. Med. Feb; 6(2): 72-81, 2000.
Moon et al., "Target site search and effective inhibition of leukaemic cell growth by a covalently closed multiple antisense Aigoriucleotide to c-myb." Biochem. J., Mar. 1:346 Pt 2: 295-303, 2000.
Van Deutekom et al., "Antisense-induced exon skipping restores dystrophin expression in DMD patient derived muscle cells." Human Molecular Genetics, 10(15): 1547-54, 2001.
Mann et al., "Antisense-induced exon skipping and synthesis of dystrophin in the mdx mouse." Proc. Natl. Acad. Sci. USA, Jan. 2: 98(1): 42-7, 2001.

* cited by examiner dystrophin (ex.31-32)     dystrophin (ex.77-79)

DL279.1 x AON#8

DL279.1

SEQUENCE LISTING

```
<160> NUMBER OF SEQ ID NOS: 36

<210> SEQ ID NO 1
<211> LENGTH: 16
<212> TYPE: DNA
<213> ORGANISM: Mouse

<400> SEQUENCE: 1
gcaatgttat ctgctt                                              16

<210> SEQ ID NO 2
<211> LENGTH: 16
<212> TYPE: DNA
<213> ORGANISM: Mouse

<400> SEQUENCE: 2
gttatctgct tcttcc                                              16

<210> SEQ ID NO 3
<211> LENGTH: 14
```

```
<212> TYPE: DNA
<213> ORGANISM: Mouse

<400> SEQUENCE: 3
tgcttcttcc agcc                                                        14

<210> SEQ ID NO 4
<211> LENGTH: 15
<212> TYPE: DNA
<213> ORGANISM: Mouse

<400> SEQUENCE: 4
tctgcttctt ccagc                                                       15

<210> SEQ ID NO 5
<211> LENGTH: 20
<212> TYPE: DNA
<213> ORGANISM: Mouse

<400> SEQUENCE: 5
gttatctgct tcttccagcc                                                  20

<210> SEQ ID NO 6
<211> LENGTH: 16
<212> TYPE: DNA
<213> ORGANISM: Mouse

<400> SEQUENCE: 6
cttttagctg ctgctc                                                      16

<210> SEQ ID NO 7
<211> LENGTH: 20
<212> TYPE: DNA
<213> ORGANISM: Mouse

<400> SEQUENCE: 7
gttgttcttt tagctgctgc                                                  20

<210> SEQ ID NO 8
<211> LENGTH: 15
<212> TYPE: DNA
<213> ORGANISM: Mouse

<400> SEQUENCE: 8
ttagctgctg ctcat                                                       15

<210> SEQ ID NO 9
<211> LENGTH: 20
<212> TYPE: DNA
<213> ORGANISM: Mouse

<400> SEQUENCE: 9
tttagctgct gctcatctcc                                                  20

<210> SEQ ID NO 10
<211> LENGTH: 15
<212> TYPE: DNA
<213> ORGANISM: Mouse

<400> SEQUENCE: 10
ctgctgctca tctcc                                                       15

<210> SEQ ID NO 11
<211> LENGTH: 15
```

<212> TYPE: DNA
<213> ORGANISM: Human

<400> SEQUENCE: 11
ctgcttcctc caacc                                                    15

<210> SEQ ID NO 12
<211> LENGTH: 20
<212> TYPE: DNA
<213> ORGANISM: Human

<400> SEQUENCE: 12
gttatctgct tcctccaacc                                               20

<210> SEQ ID NO 13
<211> LENGTH: 20
<212> TYPE: DNA
<213> ORGANISM: Human

<400> SEQUENCE: 13
gcttttcttt tagttgctgc                                               20

<210> SEQ ID NO 14
<211> LENGTH: 15
<212> TYPE: DNA
<213> ORGANISM: Human

<400> SEQUENCE: 14
ttagttgctg ctctt                                                    15

<210> SEQ ID NO 15
<211> LENGTH: 15
<212> TYPE: DNA
<213> ORGANISM: Human

<400> SEQUENCE: 15
ttgctgctct tttcc                                                    15

<210> SEQ ID NO 16
<211> LENGTH: 19
<212> TYPE: DNA
<213> ORGANISM: Human

<400> SEQUENCE: 16
ccacaggttg tgtcaccag                                                19

<210> SEQ ID NO 17
<211> LENGTH: 21
<212> TYPE: DNA
<213> ORGANISM: Human

<400> SEQUENCE: 17
tttccttagt aaccacaggt t                                             21

<210> SEQ ID NO 18
<211> LENGTH: 17
<212> TYPE: DNA
<213> ORGANISM: Human

<400> SEQUENCE: 18
tggcatttct agtttgg                                                  17

<210> SEQ ID NO 19
<211> LENGTH: 23

```
<212> TYPE: DNA
<213> ORGANISM: Human

<400> SEQUENCE: 19
ccagagcagg tacctccaac atc                                             23

<210> SEQ ID NO 20
<211> LENGTH: 20
<212> TYPE: DNA
<213> ORGANISM: Human

<400> SEQUENCE: 20
ggtaagttct gtccaagccc                                                 20

<210> SEQ ID NO 21
<211> LENGTH: 19
<212> TYPE: DNA
<213> ORGANISM: Human

<400> SEQUENCE: 21
tcaccctctg tgattttat                                                  19

<210> SEQ ID NO 22
<211> LENGTH: 14
<212> TYPE: DNA
<213> ORGANISM: Human

<400> SEQUENCE: 22
ccctctgtga tttt                                                       14

<210> SEQ ID NO 23
<211> LENGTH: 17
<212> TYPE: DNA
<213> ORGANISM: Human

<400> SEQUENCE: 23
tcacccacca tcaccct                                                    17

<210> SEQ ID NO 24
<211> LENGTH: 20
<212> TYPE: DNA
<213> ORGANISM: Human

<400> SEQUENCE: 24
tgatatcctc aaggtcaccc                                                 20

<210> SEQ ID NO 25
<211> LENGTH: 21
<212> TYPE: DNA
<213> ORGANISM: Human

<400> SEQUENCE: 25
ctgcttgatg atcatctcgt t                                               21

<210> SEQ ID NO 26
<211> LENGTH: 20
<212> TYPE: DNA
<213> ORGANISM: Human

<400> SEQUENCE: 26
tatcctctga atgtcgcatc                                                 20

<210> SEQ ID NO 27
<211> LENGTH: 20
```

```
<212> TYPE: DNA
<213> ORGANISM: Human

<400> SEQUENCE: 27
ggttatcctc tgaatgtcgc                                            20

<210> SEQ ID NO 28
<211> LENGTH: 18
<212> TYPE: DNA
<213> ORGANISM: Human

<400> SEQUENCE: 28
tctgttaggg tctgtgcc                                              18

<210> SEQ ID NO 29
<211> LENGTH: 19
<212> TYPE: DNA
<213> ORGANISM: Human

<400> SEQUENCE: 29
ccatctgtta gggtctgtg                                             19

<210> SEQ ID NO 30
<211> LENGTH: 17
<212> TYPE: DNA
<213> ORGANISM: Human

<400> SEQUENCE: 30
gtctgtgcca atatgcg                                               17

<210> SEQ ID NO 31
<211> LENGTH: 20
<212> TYPE: DNA
<213> ORGANISM: Human

<400> SEQUENCE: 31
tctgtgccaa tatgcgaatc                                            20

<210> SEQ ID NO 32
<211> LENGTH: 15
<212> TYPE: DNA
<213> ORGANISM: Human

<400> SEQUENCE: 32
tgtctcaagt tcctc                                                 15

<210> SEQ ID NO 33
<211> LENGTH: 20
<212> TYPE: DNA
<213> ORGANISM: Human

<400> SEQUENCE: 33
gaattaaatg tctcaagttc                                            20

<210> SEQ ID NO 34
<211> LENGTH: 18
<212> TYPE: DNA
<213> ORGANISM: Human

<400> SEQUENCE: 34
ttaaatgtct caagttcc                                              18

<210> SEQ ID NO 35
<211> LENGTH: 16
```

```
<212> TYPE: DNA
<213> ORGANISM: Human

<400> SEQUENCE: 35
gtagttccct ccaacg                                                    16

<210> SEQ ID NO 36
<211> LENGTH: 15
<212> TYPE: DNA
<213> ORGANISM: Human

<400> SEQUENCE: 36
catgtagttc cctcc                                                     15
```

INDUCTION OF EXON SKIPPING IN EUKARYOTIC CELLS

CROSS REFERENCE TO RELATED APPLICATIONS

This application is a continuation of International Application PCT/NL01/00697, filed Sep. 21, 2001, designating the United States, published in English Mar. 28, 2002, as WO 02/024906 A1 and subsequently published with corrections Jan. 23, 2003, as WO 02/024906 C2, the contents of both of which are incorporated by this reference.

TECHNICAL FIELD

The invention relates to the field of gene therapy.

BACKGROUND

Given the rapid advances of human genome research, professionals and the public expect that the near future will bring us, in addition to understanding of disease mechanisms and refined and reliable diagnostics, therapies for many devastating genetic diseases.

While it is hoped that for some (e.g., metabolic) diseases, the improved insights will bring easily administrable small-molecule therapies, it is likely that in most cases one or another form of gene therapy will ultimately be required, i.e., the correction, addition or replacement of the defective gene product.

In the past few years, research and development in this field have highlighted several technical difficulties which need to be overcome, e.g., related to the large size of many genes involved in genetic disease (limiting the choice of suitable systems to administer the therapeutic gene), the accessibility of the tissue in which the therapeutic gene should function (requiring the design of specific targeting techniques, either physically, by restricted injection, or biologically, by developing systems with tissue-specific affinities) and the safety to the patient of the administration system. These problems are to some extent interrelated, and it can be generally concluded that the smaller the therapeutic agent is, the easier it will become to develop efficient, targetable and safe administration systems.

BRIEF SUMMARY OF THE INVENTION

The present invention addresses this problem by inducing so-called exon-skipping in cells. Exon-skipping results in mature mRNA that does not contain the skipped exon and thus, when the exon codes for amino acids, can lead to the expression of an altered product. Technology for exon-skipping is currently directed toward the use of so-called "Antisense Oligonucleotides" (AONs).

Much of this work is done in the mdx mouse model for Duchenne muscular dystrophy (DMD). The mdx mouse, which carries a nonsense mutation in exon 23 of the dystrophin gene, has been used as an animal model of Duchenne muscular dystrophy. Despite the mdx mutation, which should preclude the synthesis of a functional dystrophin protein, rare, naturally occurring dystrophin-positive fibers have been observed in mdx muscle tissue. These dystrophin-positive fibers are thought to have arisen from an apparently naturally occurring exon-skipping mechanism, either due to somatic mutations or through alternative splicing.

AONs directed to, respectively, the 3' and 5' splice sites of introns 22 and 23 in dystrophin pre-mRNA have been shown to interfere with factors normally involved in removal of intron 23 so that exon 23 was also removed from the mRNA (Wilton, 1999). In a similar study, Dunckley et al. (1998) showed that exon skipping using AONs directed to 3' and 5' splice sites can have unexpected results. They observed skipping of not only exon 23 but also of exons 24-29, thus resulting in an mRNA containing an exon 22-exon 30 junction.

The underlying mechanism for the appearance of the unexpected 22-30 splicing variant is not known. It could be due to the fact that splice sites contain consensus sequences leading to promiscuous hybridization of the oligos used to direct the exon skipping. Hybridization of the oligos to other splice sites than the sites of the exon to be skipped of course could easily interfere with the accuracy of the splicing process. On the other hand, the accuracy could be lacking due to the fact that two oligos (for the 5' and the 3' splice site) need to be used. Pre-mRNA containing one but not the other oligo could be prone to unexpected splicing variants.

To overcome these and other problems, the present invention provides a method for directing splicing of a pre-mRNA in a system capable of performing a splicing operation comprising contacting the pre-mRNA in the system with an agent capable of specifically inhibiting an exon inclusion signal of at least one exon in the pre-mRNA, the method further comprising allowing splicing of the pre-mRNA. Interfering with an exon inclusion signal (EIS) has the advantage that such elements are located within the exon. By providing an antisense oligo for the interior of the exon to be skipped, it is possible to interfere with the exon inclusion signal, thereby effectively masking the exon from the splicing apparatus. The failure of the splicing apparatus to recognize the exon to be skipped thus leads to exclusion of the exon from the final mRNA.

The present invention does not interfere directly with the enzymatic process of the splicing machinery (the joining of the exons). It is thought that this allows the method to be more robust and reliable. It is thought that an EIS is a particular structure of an exon that allows splice acceptor and donor to assume a particular spatial conformation. In this concept, it is the particular spatial conformation that enables the splicing machinery to recognize the exon. However, the invention is certainly not limited to this model.

It has been found that agents capable of binding to an exon can inhibit an EIS. Agents may specifically contact the exon at any point and still be able to specifically inhibit the EIS. The mRNA may be useful in itself. For instance, production of an undesired protein can be at least in part reduced by inhibiting inclusion of a required exon into the mRNA. A preferred method of the invention further comprises allowing translation of mRNA produced from splicing of the pre-mRNA. Preferably, the MRNA encodes a functional protein. In a preferred embodiment, the protein comprises two or more domains, wherein at least one of the domains is encoded by the mRNA as a result of skipping of at least part of an exon in the pre-mRNA.

Exon skipping will typically, though not necessarily, be of relevance for proteins in the wild type configuration, having at least two functional domains that each performs a function, wherein the domains are generated from distinct parts of the primary amino acid sequence. Examples are, for instance, transcription factors. Typically, these factors comprise a DNA binding domain and a domain that interacts with other proteins in the cell. Skipping of an exon that encodes a part of the primary amino acid sequence that lies between these two domains can lead to a shorter protein that comprises the same function, at least in part. Thus, detrimental mutations in this intermediary region (for instance, frame-shift or stop mutations) can be at least in part repaired by inducing exon skipping to allow synthesis of the shorter (partly) functional protein.

Using a method of the invention, it is also possible to induce partial skipping of the exon. In this embodiment, the contacting results in activation of a cryptic splice site in a contacted exon. This embodiment broadens the potential for manipulation of the pre-mRNA leading to a functional protein. Preferably, the system comprises a cell. Preferably, the cell is cultured in vitro or in the organism in vivo. Typically, though not necessarily, the organism comprises a human or a mouse.

In a preferred embodiment, the invention provides a method for at least in part decreasing the production of an aberrant protein in a cell, the cell comprising pre-mRNA comprising exons coding for the protein, the method comprising providing the cell with an agent capable of specifically inhibiting an exon inclusion signal of at least one of the exons, the method further comprising allowing translation of mRNA produced from splicing of the pre-mRNA.

Any agent capable of specifically inhibiting an exon exclusion signal can be used for the present invention. Preferably, the agent comprises a nucleic acid or a functional equivalent thereof. Preferably, but not necessarily, the nucleic acid is in single-stranded form. Peptide nucleic acid and other molecules comprising the same nucleic acid binding characteristics in kind, but not necessarily in amount, are suitable equivalents. Nucleic acid or an equivalent may comprise modifications to provide additional functionality. For instance, 2'-O-methyl oligoribonucleotides can be used. These ribonucleotides are more resistant to RNAse action than conventional oligonucleotides.

In a preferred embodiment of the invention, the exon inclusion signal is interfered with by an antisense nucleic acid directed to an exon recognition sequence (ERS). These sequences are relatively purine-rich and can be distinguished by scrutinizing the sequence information of the exon to be skipped (Tanaka et al., 1994, Mol. Cell. Biol. 14, p. 1347-1354). Exon recognition sequences are thought to aid inclusion into mRNA of so-called weak exons (Achsel et al., 1996, J. Biochem. 120, p. 53-60). These weak exons comprise, for instance, 5' and or 3' splice sites that are less efficiently recognized by the splicing machinery. In the present invention, it has been found that exon skipping can also be induced in so-called strong exons, i.e., exons which are normally efficiently recognized by the splicing machinery of the cell. From any given sequence, it is (almost) always possible to predict whether the sequence comprises putative exons and to determine whether these exons are strong or weak. Several algorithms for determining the strength of an exon exist. A useful algorithm can be found on the NetGene2 splice site prediction server (Brunak, et al., 1991, J. Mol. Biol. 220, p. 49-65). Exon skipping by a means of the invention can be induced in (almost) every exon, independent of whether the exon is a weak exon or a strong exon and also independent of whether the exon comprises an ERS. In a preferred embodiment, an exon that is targeted for skipping is a strong exon. In another preferred embodiment, an exon targeted for skipping does not comprise an ERS.

Methods of the invention can be used in many ways. In one embodiment, a method of the invention is used to at least in part decrease the production of an aberrant protein. Such proteins can, for instance, be onco-proteins or viral proteins. In many tumors, not only the presence of an onco-protein but also its relative level of expression has been associated with the phenotype of the tumor cell. Similarly, not only the presence of viral proteins but also the amount of viral protein in a cell determines the virulence of a particular virus. Moreover, for efficient multiplication and spread of a virus, the timing of expression in the life cycle and the balance in the amount of certain viral proteins in a cell determines whether viruses are efficiently or inefficiently produced. Using a method of the invention, it is possible to lower the amount of aberrant protein in a cell such that, for instance, a tumor cell becomes less tumorigenic (metastatic) and/or a virus-infected cell produces less virus.

In a preferred embodiment, a method of the invention is used to modify the aberrant protein into a functional protein. In one embodiment, the functional protein is capable of performing a function of a protein normally present in a cell but absent in the cells to be treated. Very often, even partial restoration of function results in significantly improved performance of the cell thus treated. Due to the better performance, such cells can also have a selective advantage over unmodified cells, thus aiding the efficacy of the treatment.

This aspect of the invention is particularly suited for the restoration of expression of defective genes. This is achieved by causing the specific skipping of targeted exons, thus bypassing or correcting deleterious mutations (typically stop-mutations or frame-shifting point mutations, single- or multi-exon deletions or insertions leading to translation termination).

Compared to gene-introduction strategies, this novel form of splice-modulation gene therapy requires the administration of much smaller therapeutic reagents, typically, but not limited to, 14-40 nucleotides. In a preferred embodiment, molecules of 14-25 nucleotides are used since these molecules are easier to produce and enter the cell more effectively. The methods of the invention allow much more flexibility in the subsequent design of effective and safe administration systems. An important additional advantage of this aspect of the invention is that it restores (at least some of) the activity of the endogenous gene, which still possesses most or all of its gene-regulatory circuitry, thus ensuring proper expression levels and the synthesis of tissue-specific isoforms.

This aspect of the invention can in principle be applied to any genetic disease or genetic predisposition to disease in which targeted skipping of specific exons would restore the translational reading frame when this has been disrupted by the original mutation, provided that translation of an internally slightly shorter protein is still fully or partly functional. Preferred embodiments for which this application can be of therapeutic value are: predisposition to second hit mutations in tumor suppressor genes, e.g., those involved in breast cancer, colon cancer, tuberous sclerosis, neurofibromatosis etc., where (partial) restoration of activity would preclude the manifestation of nullosomy by second hit mutations and thus would protect against tumorigenesis. Another preferred embodiment involves the (partial) restoration of defective gene products which have a direct disease causing effect, e.g., hemophilia A (clotting factor VIII deficiency), some forms of congenital hypothyroidism (due to thyroglobulin synthesis deficiency) and Duchenne muscular dystrophy (DMD), in which frame-shifting deletions, duplications and stop mutations in the X-linked dystrophin gene cause severe, progressive muscle degradation. DMD is typically lethal in late adolescence or early adulthood, while non-frame-shifting deletions or duplications in the same gene cause the much milder Becker muscular dystrophy (BMD), compatible with a life expectancy between 35-40 years to normal. In the embodiment as applied to DMD, the present invention enables exon skipping to extend an existing deletion (or alter the MRNA product of an existing duplication) by as many adjacent exons as required to restore the reading frame and generate an internally slightly shortened, but still functional, protein. Based on the much milder clinical symptoms of BMD patients with the equivalent of this induced deletion, the disease in the DMD patients would have a much milder course after AON-therapy.

Many different mutations in the dystrophin gene can lead to a dysfunctional protein. (For a comprehensive inventory see www.dmd.nl, the internationally accepted database for DMD and related disorders.) The precise exon to be skipped to generate a functional dystrophin protein varies from mutation to mutation. Table 1 comprises a non-limiting list of exons that can be skipped and lists for the mentioned exons some of the more frequently occurring dystrophin gene mutations that have been observed in humans and that can be treated with a method of the invention. Skipping of the mentioned exon leads to a mutant dystrophin protein comprising at least the functionality of a Becker mutant. Thus, in one embodiment, the invention provides a method of the invention wherein the exon inclusion signal is present in exon numbers 2, 8, 19, 29, 43, 44, 45, 46, 50, 51, 52 or 53 of the human dystrophin gene. The occurrence of certain deletion/insertion variations is more frequent than others. In the present invention, it was found that by inducing skipping of exon 46 with a means or a method of the invention, approximately 7% of DMD-deletion containing patients can be treated, resulting in the patients to comprise dystrophin-positive muscle fibers. By inducing skipping of exon 51, approximately 15% of DMD-deletion containing patients can be treated with a means or method of the invention. Such treatment will result in the patient having at least some dystrophin-positive fibers. Thus, with either skipping of exon 46 or 51 using a method of the invention, approximately 22% of the patients containing a deletion in the dystrophin gene can be treated. Thus, in a preferred embodiment of the invention, the exon exclusion signal is present in exon 46 or exon 51. In a particularly preferred embodiment, the agent comprises a nucleic acid sequence according to hAON#4, hAON#6, hAON#8, hAON#9, hAON#11 and/or one or more of hAON#21-30 or a functional part, derivative and/or analogue of the hAON. A functional part, derivative and/or analogue of the hAON comprises the same exon skipping activity in kind, but not necessarily in amount, in a method of the invention.

TABLE 1

| Exon to be skipped | Therapeutic for DMD-deletions (exons) | Frequency in www.dmd.nl (%) |
|---|---|---|
| 2 | 3-7 | 2 |
| 8 | 3-7 | 4 |
|   | 4-7 |   |
|   | 5-7 |   |
|   | 6-7 |   |
| 43 | 44 | 5 |
|   | 44-47 |   |
| 44 | 35-43 | 8 |
|   | 45 |   |
|   | 45-54 |   |
| 45 | 18-44 | 13 |
|   | 46-47 |   |
|   | 44 |   |
|   | 46-48 |   |
|   | 46-49 |   |
|   | 46-51 |   |
|   | 46-53 |   |
| 46 | 45 | 7 |
| 50 | 51 | 5 |
|   | 51-55 |   |
| 51 | 50 | 15 |
|   | 45-50 |   |

TABLE 1-continued

| Exon to be skipped | Therapeutic for DMD-deletions (exons) | Frequency in www.dmd.nl (%) |
|---|---|---|
|   | 48-50 |   |
|   | 49-50 |   |
|   | 52 |   |
|   | 52-63 |   |
| 52 | 51 | 3 |
|   | 53 |   |
|   | 53-55 |   |
| 53 | 45-52 | 9 |
|   | 48-52 |   |
|   | 49-52 |   |
|   | 50-52 |   |
|   | 52 |   |

It can be advantageous to induce exon skipping of more than one exon in the pre-mRNA. For instance, considering the wide variety of mutations and the fixed nature of exon lengths and amino acid sequence flanking such mutations, the situation can occur that for restoration of function more than one exon needs to be skipped. A preferred but non-limiting example of such a case in the DMD deletion database is a 46-50 deletion. Patients comprising a 46-50 deletion do not produce functional dystrophin. However, an at least partially functional dystrophin can be generated by inducing skipping of both exon 45 and exon 51. Another preferred but non-limiting example is patients comprising a duplication of exon 2. By providing one agent capable of inhibiting an EIS of exon 2, it is possible to partly skip either one or both exons 2, thereby regenerating the wild-type protein next to the truncated or double exon 2 skipped protein. Another preferred but non-limiting example is the skipping of exons 45 through 50. This generates an in-frame Becker-like variant. This Becker-like variant can be generated to cure any mutation localized in exons 45, 46, 47, 48, 49, and/or 50 or combinations thereof. In one aspect, the invention therefore provides a method of the invention further comprising providing the cell with another agent capable of inhibiting an exon inclusion signal in another exon of the pre-mRNA. Of course, it is completely within the scope of the invention to use two or more agents for the induction of exon skipping in pre-mRNA of two or more different genes.

In another aspect, the invention provides a method for selecting the suitable agents for splice-therapy and their validation as specific exon-skipping agents in pilot experiments. A method is provided for determining whether an agent is capable of specifically inhibiting an exon inclusion signal of an exon, comprising providing a cell having a pre-mRNA containing the exon with the agent, culturing the cell to allow the formation of an mRNA from the pre-mRNA and determining whether the exon is absent the mRNA. In a preferred embodiment, the agent comprises a nucleic acid or a functional equivalent thereof, the nucleic acid comprising complementarity to a part of the exon. Agents capable of inducing specific exon skipping can be identified with a method of the invention. It is possible to include a prescreen for agents by first identifying whether the agent is capable of binding with a relatively high affinity to an exon containing nucleic acid, preferably RNA. To this end, a method for determining whether an agent is capable of specifically inhibiting an exon inclusion signal of an exon is provided, further comprising first determining in vitro the relative binding affinity of the nucleic acid or functional equivalent thereof to an RNA molecule comprising the exon.

In yet another aspect, an agent is provided that is obtainable by a method of the invention. In a preferred embodiment, the agent comprises a nucleic acid or a functional equivalent thereof. Preferably the agent, when used to induce exon skipping in a cell, is capable of at least in part reducing the amount of aberrant protein in the cell. More preferably, the exon skipping results in an mRNA encoding a protein that is capable of performing a function in the cell. In a particularly preferred embodiment, the pre-mRNA is derived from a dystrophin gene. Preferably, the functional protein comprises a mutant or normal dystrophin protein. Preferably, the mutant dystrophin protein comprises at least the functionality of a dystrophin protein in a Becker patient. In a particularly preferred embodiment, the agent comprises the nucleic acid sequence of hAON#4, hAON#6, hAON#8, hAON#9, hAON#11 and/or one or more of hAON#21-30 or a functional part, derivative and/or analogue of the hAON. A functional part, derivative and/or analogue of the hAON comprises the same exon skipping activity in kind, but not necessarily in amount, in a method of the invention.

The art describes many ways to deliver agents to cells. Particularly, nucleic acid delivery methods have been widely developed. The artisan is well capable of determining whether a method of delivery is suitable for performing the present invention. In a non-limiting example, the method includes the packaging of an agent of the invention into liposomes, the liposomes being provided to cells comprising a target pre-mRNA. Liposomes are particularly suited for delivery of nucleic acid to cells. Antisense molecules capable of inducing exon skipping can be produced in a cell upon delivery of nucleic acid containing a transcription unit to produce antisense RNA. Non-limiting examples of suitable transcription units are small nuclear RNA (SNRP) or tRNA transcription units. The invention, therefore, further provides a nucleic acid delivery vehicle comprising a nucleic acid or functional equivalent thereof of the invention capable of inhibiting an exon inclusion signal. In one embodiment, the delivery vehicle is capable of expressing the nucleic acid of the invention. Of course, in case, for instance, single-stranded viruses are used as a vehicle, it is entirely within the scope of the invention when such a virus comprises only the antisense sequence of an agent of the invention. In another embodiment of single strand viruses, AONs of the invention are encoded by small nuclear RNA or tRNA transcription units on viral nucleic encapsulated by the virus as vehicle. A preferred single-stranded virus is adeno-associated virus.

In yet another embodiment, the invention provides the use of a nucleic acid or a nucleic acid delivery vehicle of the invention for the preparation of a medicament. In a preferred embodiment, the medicament is used for the treatment of an inherited disease. More preferably, the medicament is used for the treatment of Duchenne Muscular Dystrophy.

BRIEF DESCRIPTION OF THE DRAWINGS

FIG. 4A. RT-PCR analysis showed a truncated product, of which the size corresponded to exon 45 directly spliced to exon 47, in the mouse cell cultures upon transfection with the different mAONs#4, 6, 9, and 11. No exon 46 skipping was detected following transfection with a random AON.

FIG. 4B. RT-PCR analysis in the human muscle cell cultures derived from one unaffected individual (C) and two unrelated DMD patients (P1 and P2) revealed truncated products upon transfection with hAON#4 and hAON#8. In the control, this product corresponded to exon 45 spliced to exon 47, while in the patients, the fragment size corresponded to exon 44 spliced to exon 47. No exon 46 skipping was detected in the non-transfected cell cultures or following transfection with a random hAON. Highest exon 46 skipping efficiencies were obtained with hAON#8.

DETAILED DESCRIPTION OF THE INVENTION

Examples

Example 1

Figure 1:
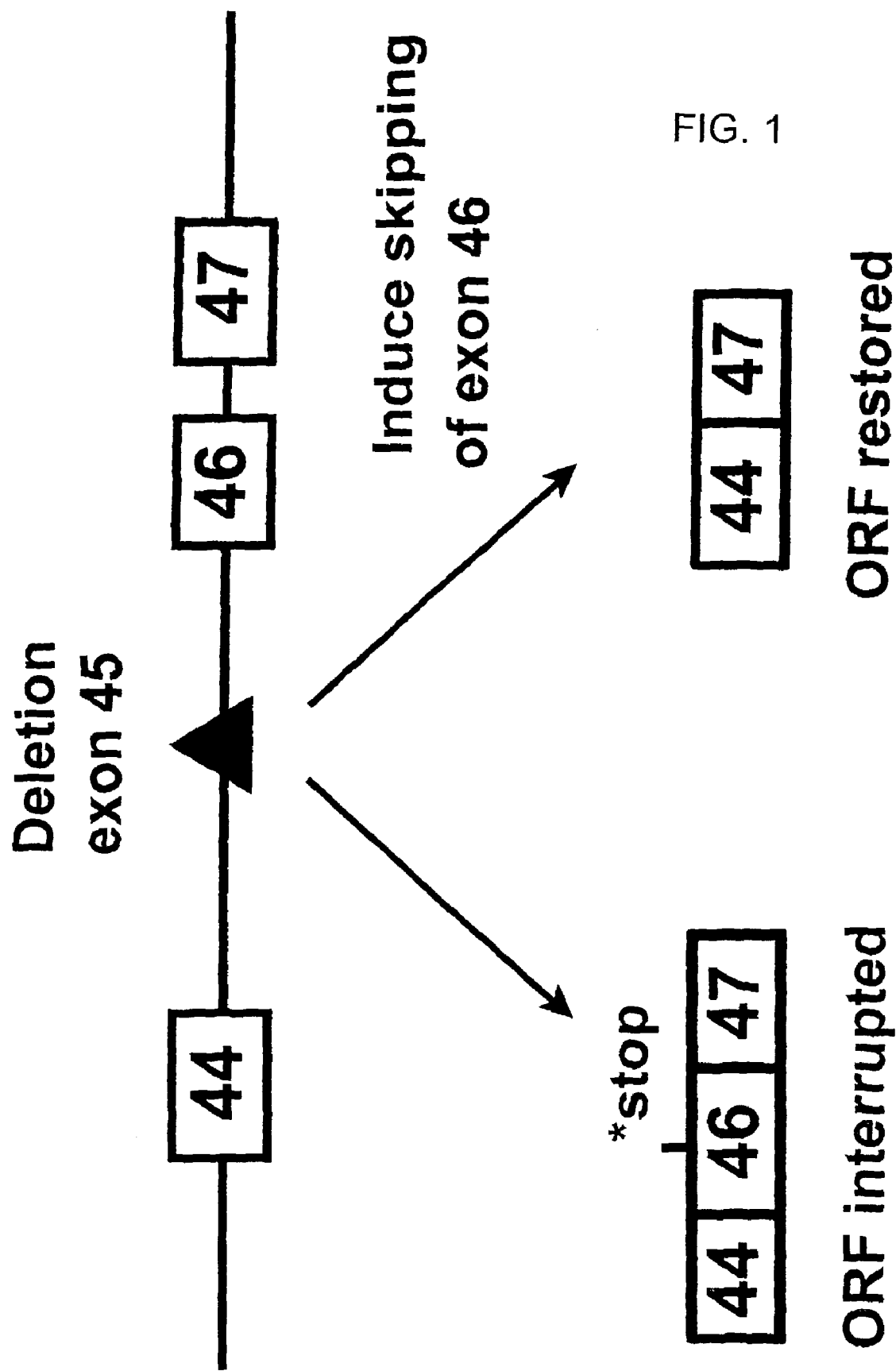
FIG. 1. Deletion of exon 45 is one of the most frequent DMD-mutations. Due to this deletion, exon 44 is spliced to exon 46, the translational reading frame is interrupted, and a stop codon is created in exon 46 leading to a dystrophin deficiency. Our aim is to artificially induce the skipping of an additional exon, exon 46, in order to reestablish the reading frame and restore the synthesis of a slightly shorter, but largely functional, dystrophin protein as found in the much milder affected Becker muscular dystrophy patients affected by a deletion of both exons 45 and 46.

Since exon 45 is one of the most frequently deleted exons in DMD, we initially aimed at inducing the specific skipping of exon 46 (FIG. 1). This would produce the shorter, largely functional dystrophin found in BMD patients carrying a deletion of exons 45 and 46. The system was initially set up for modulation of dystrophin pre-mRNA splicing of the mouse dystrophin gene. We later aimed for the human dystrophin gene with the intention to restore the translational reading frame and dystrophin synthesis in muscle cells from DMD patients affected by a deletion of exon 45.

Design of mAONs and hAONs

Figure 2:
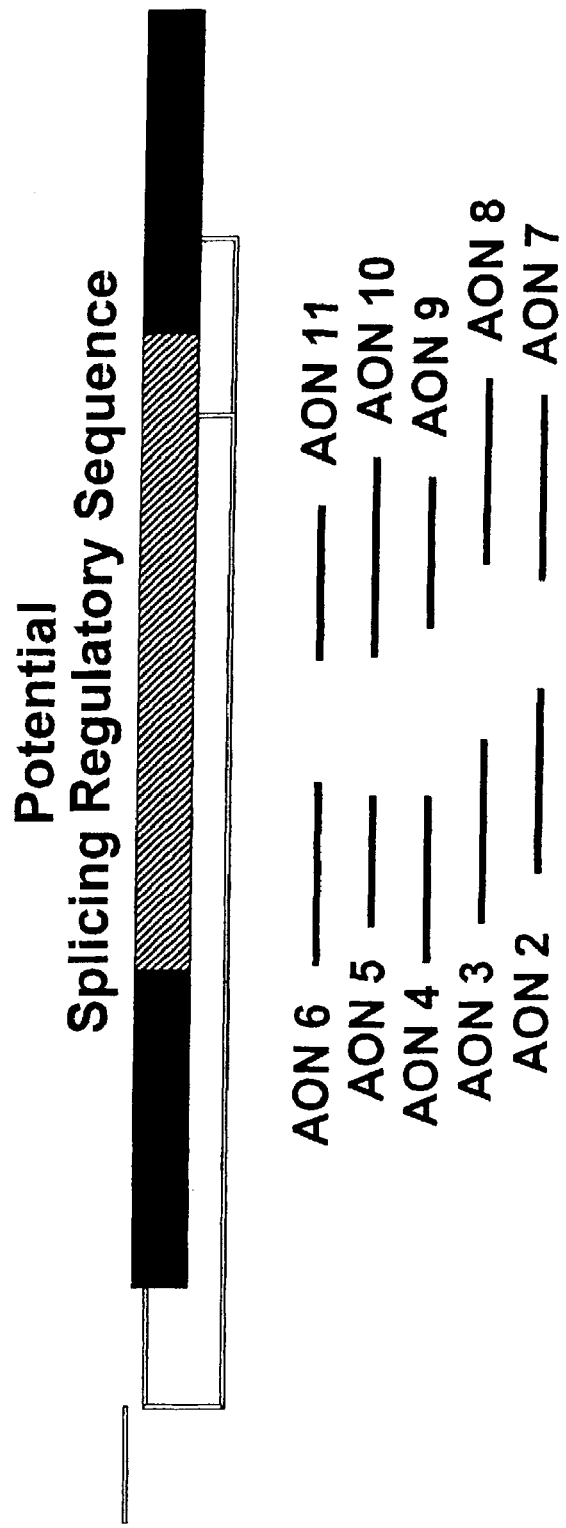
FIG. 2. Exon 46 contains a purine-rich region that is hypothesized to have a potential role in the regulation of its splicing in the pre-mRNA. A series of overlapping 2'O-methyl phosphorothioate antisense oligoribonucleotides (AONs) was designed directed at this purine-rich region in mouse dystrophin exon 46. The AONs differ both in length and sequence. The chemical modifications render the AONs resistant to endonucleases and RNaseH inside the muscle cells. To determine the transfection efficiency in our in vitro studies, the AONs contained a 5' fluorescein group which allowed identification of AON-positive cells.

A series of mouse- and human-specific AONs (mAONs and hAONs) was designed, directed at an internal part of exon 46 that contains a stretch of purine-rich sequences and is hypothesized to have a putative regulatory role in the splicing process of exon 46 (FIG. 2). For the initial screening of the AONs in the gel mobility shift assays (see below), we used non-modified DNA-oligonucleotides (synthesized by Euro-Gentec, Belgium). For the actual transfection experiments in muscle cells, we used 2'-O-methyl-phosphorothioate oligoribonucleotides (also synthesized by EuroGentec, Belgium). These modified RNA oligonucleotides are known to be resistant to endonucleases and RNaseH, and to bind to RNA with high affinity. The sequences of those AONs that were eventually effective and applied in muscle cells in vitro are shown below. The corresponding mouse and human-specific AONs are highly homologous but not completely identical.

The listing below refers to the deoxy-form used for testing, in the finally used 2-O-methyl ribonucleotides all T's should be read as U's.

| | | | |
|---|---|---|---|
| mAON#2: | 5' | GCAATGTTATCTGCTT | (SEQ ID NO: 1) |
| mAON#3: | 5' | GTTATCTGCTTCTTCC | (SEQ ID NO: 2) |
| mAON#4: | 5' | CTGCTTCTTCCAGCC | (SEQ ID NO: 3) |
| mAON#5: | 5' | TCTGCTTCTTCCAGC | (SEQ ID NO: 4) |
| mAON#6: | 5' | GTTATCTGCTTCTTCCAGCC | (SEQ ID NO: 5) |
| mAON#7: | 5' | CTTTTAGCTGCTGCTC | (SEQ ID NO: 6) |
| mAON#8: | 5' | GTTGTTCTTTTAGCTGCTGC | (SEQ ID NO: 7) |
| mAON#9: | 5' | TTAGCTGCTGCTCAT | (SEQ ID NO: 8) |
| mAON#10: | 5' | TTTAGCTGCTGCTCATCTCC | (SEQ ID NO: 9) |
| mAON#11: | 5' | CTGCTGCTCATCTCC | (SEQ ID NO: 10) |
| hAON#4: | 5' | CTGCTTCCTCCAACC | (SEQ ID NO: 11) |
| hAON#6: | 5' | GTTATCTGCTTCCTCCAACC | (SEQ ID NO: 12) |
| hAON#8: | 5' | GCTTTTCTTTTAGTTGCTGC | (SEQ ID NO: 13) |
| hAON#9: | 5' | TTAGTTGCTGCTCTT | (SEQ ID NO: 14) |
| hAON#11: | 5' | TTGCTGCTCTTTTCC | (SEQ ID NO: 15) |

Gel Mobility Shift Assays

Figure 3:
FIG. 3. To determine the binding affinity of the different AONs to the target exon 46 RNA, we performed gel mobility shift assays. In this figure, the five mAONs (mAON#4, 6, 8, 9, and 11) with highest affinity for the target RNA are shown. Upon binding of the AONs to the RNA, a complex is formed that exhibits a retarded gel mobility as can be determined by the band shift. The binding of the AONs to the target was sequence-specific. A random mAON, i.e. not specific for exon 46, did not generate a band shift.

The efficacy of the AONs is determined by their binding affinity for the target sequence. Notwithstanding recent improvements in computer simulation programs for the prediction of RNA-folding, it is difficult to speculate which of the designed AONs would be capable of binding the target sequence with a relatively high affinity. Therefore, we performed gel mobility shift assays (according to protocols described by Bruice et al., 1997). The exon 46 target RNA fragment was generated by in vitro T7-transcription from a PCR fragment (amplified from either murine or human muscle mRNA using a sense primer that contains the T7 promoter sequence) in the presence of 32P-CTP. The binding affinity of the individual AONs (0.5 pmol) for the target transcript fragments was determined by hybridization at 37° C. for 30 minutes and subsequent polyacrylamide (8%) gel electrophoresis. We performed these assays for the screening of both the mouse and human-specific AONs (FIG. 3). At least 5 different mouse-specific AONs (mAON#4, 6, 8, 9 and 11) and four corresponding human-specific AONs (hAON#4, 6, 8, and 9) generated a mobility shift, demonstrating their binding affinity for the target RNA.

Transfection into Muscle Cell Cultures

The exon 46-specific AONs which showed the highest target binding affinity in gel mobility shift assays were selected for analysis of their efficacy in inducing the skipping in muscle cells in vitro. In all transfection experiments, we included a non-specific AON as a negative control for the specific skipping of exon 46. As mentioned, the system was first set up in mouse muscle cells. We used both proliferating myoblasts and post-mitotic myotube cultures (expressing higher levels of dystrophin) derived from the mouse muscle cell line C2C12. For the subsequent experiments in human-derived muscle cell cultures, we used primary muscle cell cultures isolated from muscle biopsies from one unaffected individual and two unrelated DMD patients carrying a deletion of exon 45. These heterogeneous cultures contained approximately 20-40% myogenic cells. The different AONs (at a concentration of 1 μM) were transfected into the cells using the cationic polymer PEI (MBI Fermentas) at a ratio-equivalent of 3. The AONs transfected in these experiments contained a 5' fluorescein group which allowed us to determine the transfection efficiencies by counting the number of fluorescent nuclei. Typically, more than 60% of cells showed specific nuclear uptake of the AONs. To facilitate RT-PCR analysis, RNA was isolated 24 hours post-transfection using RNAzol B (CamPro Scientific, The Netherlands).

RT-PCR and Sequence Analysis

Figure 4A:
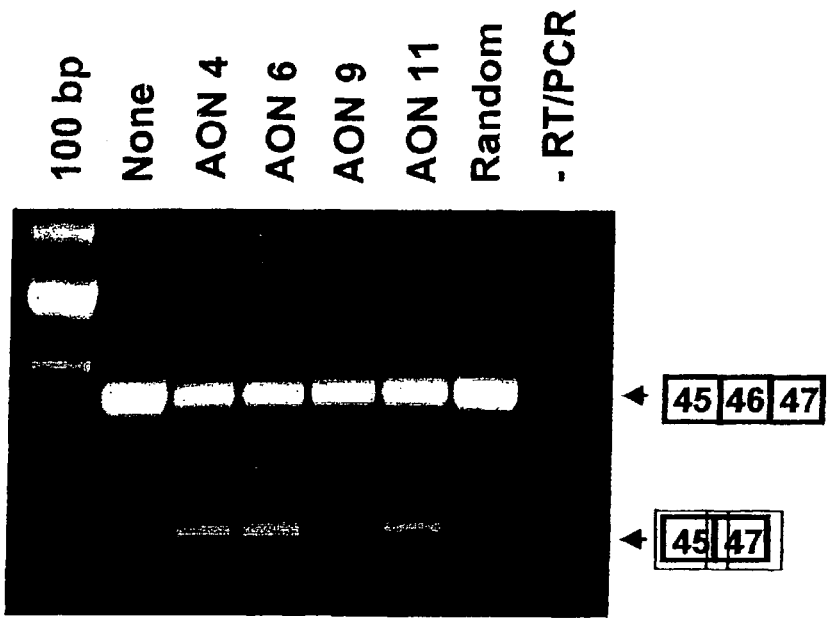
FIGS. 4A and 4B. The mouse- and human-specific AONs which showed the highest binding affinity in the gel mobility shift assays were transfected into mouse and human myotube cultures.
Figure 4B:
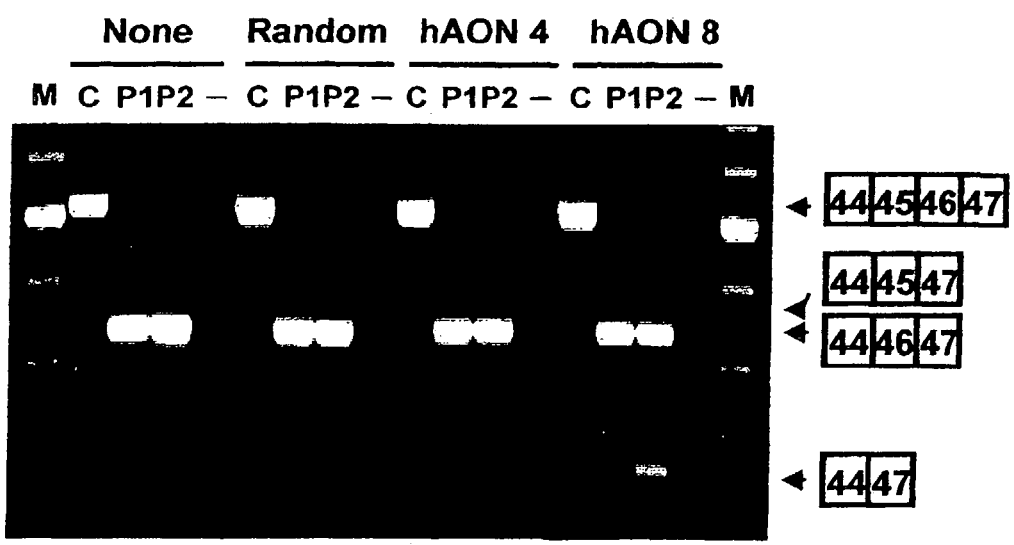

RNA was reverse transcribed using C. therm. polymerase (Roche) and an exon 48-specific reverse primer. To facilitate the detection of skipping of dystrophin exon 46, the cDNA was amplified by two rounds of PCR, including a nested amplification using primers in exons 44 and 47 (for the human system), or exons 45 and 47 (for the mouse system). In the mouse myoblast and myotube cell cultures, we detected a truncated product of which the size corresponded to exon 45 directly spliced to exon 47 (FIG. 4). Subsequent sequence analysis confirmed the specific skipping of exon 46 from these mouse dystrophin transcripts. The efficiency of exon skipping was different for the individual AONs, with mAON#4 and #11 showing the highest efficiencies. Following these promising results, we focused on inducing a similar modulation of dystrophin splicing in the human-derived muscle cell cultures. Accordingly, we detected a truncated product in the control muscle cells, corresponding to exon 45 spliced to exon 47. Interestingly, in the patient-derived muscle cells, a shorter fragment was detected, which consisted of exon 44 spliced to exon 47. The specific skipping of exon 46 from the human dystrophin transcripts was confirmed by sequence data. This splicing modulation of both the mouse and human dystrophin transcript was neither observed in non-transfected cell cultures nor in cultures transfected with a non-specific AON.

Immunohistochemical Analysis

Figure 5:
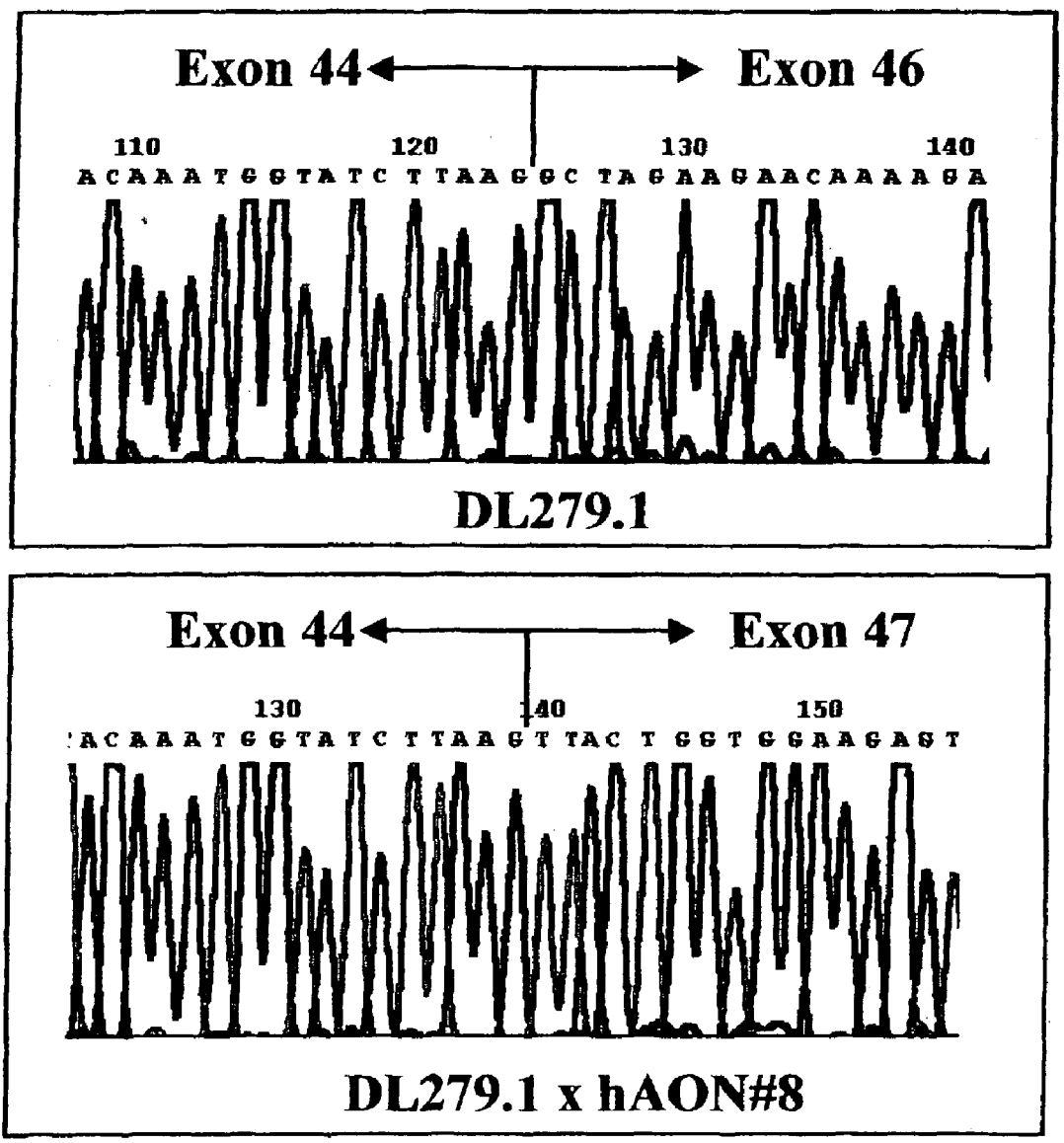
FIG. 5. Sequence data from the RT-PCR products obtained from patient DL279.1 (corresponding to P1 in FIG. 4), which confirmed the deletion of exon 45 in this patient (upper panel), and the additional skipping of exon 46 following transfection with hAON#8 (lower panel). The skipping of exon 46 was specific, and exon 44 was exactly spliced to exon 47, which reestablishes the translational reading frame.
Figure 6:
FIG. 6. Immunohistochemical analysis of the muscle cell culture from patient DL279.1 upon transfection with hAON#8. Cells were subject to two different dystrophin antibodies raised against different regions of the protein, located proximally (ManDys-1, ex. 31-32) and distally (Dys-2, ex. 77-79) from the targeted exon 46. The lower panel shows the absence of a dystrophin protein in the myotubes, whereas the hAON#8-induced skipping of exon 46 clearly restored the synthesis of a dystrophin protein as detected by both antibodies (upper panel).
Figure 6:
Figure 6:
Figure 6:

We intended to induce the skipping of exon 46 in muscle cells from patients carrying an exon 45 deletion in order to restore the translation and synthesis of a dystrophin protein. To detect a dystrophin product upon transfection with hAON#8, the two patient-derived muscle cell cultures were subject to immunocytochemistry using two different dystrophin monoclonal antibodies (Mandys-1 and Dys-2) raised against domains of the dystrophin protein located proximal and distal of the targeted region respectively. Fluorescent analysis revealed restoration of dystrophin synthesis in both patient-derived cell cultures (FIG. 5). Approximately at least 80% of the fibers stained positive for dystrophin in the treated samples.

Our results show, for the first time, the restoration of dystrophin synthesis from the endogenous DMD gene in muscle cells from DMD patients. This is a proof of principle of the feasibility of targeted modulation of dystrophin pre-mRNA splicing for therapeutic purposes.

Targeted Skipping of Exon 51
Simultaneous Skipping of Dystrophin Exons

The targeted skipping of exon 51. We demonstrated the feasibility of AON-mediated modulation of dystrophin exon 46 splicing, in mouse and human muscle cells in vitro. These findings warranted further studies to evaluate AONs as therapeutic agents for DMD. Since most DMD-causing deletions are clustered in two mutation hot spots, the targeted skipping of one particular exon can restore the reading frame in series of patients with different mutations (see Table 1). Exon 51 is an interesting target exon. The skipping of this exon is therapeutically applicable in patients carrying deletions spanning exon 50, exons 45-50, exons 48-50, exons 49-50, exon 52, and exons 52-63, which includes a total of 15% of patients from our Leiden database.

Figure 7A:
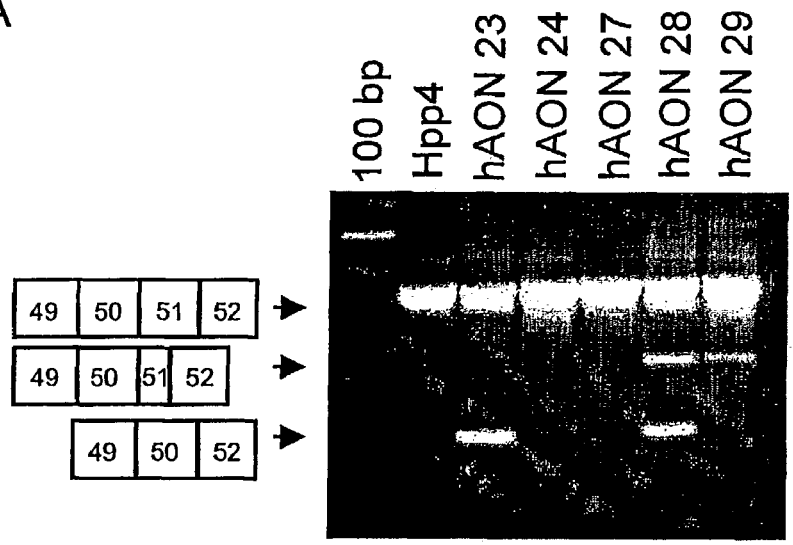
FIG. 7A. RT-PCR analysis of RNA isolated from human control muscle cell cultures treated with hAON#23, #24, #27, #28, or #29. An additional aberrant splicing product was obtained in cells treated with hAON#28 and #29. Sequence analysis revealed the utilization of an in-frame cryptic splice site within exon 51 that is used at a low frequency upon AON treatment. The product generated included a partial exon 51, which also had a restored reading frame, thereby confirming further the therapeutic value.
Figure 7B:
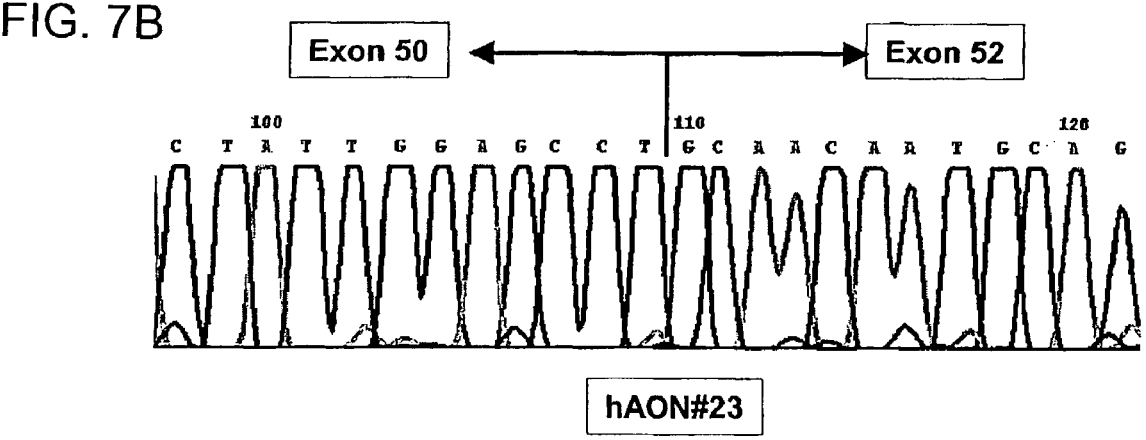
FIG. 7B. A truncated product, with a size corresponding to exon 50 spliced to exon 52, was detected in cells treated with hAON#23 and #28. Sequence analysis of these products confirmed the precise skipping of exon 51.

We designed a series of ten human-specific AONs (hAON#21-30, see below) directed at different purine-rich regions within dystrophin exon 51. These purine-rich stretches suggested the presence of a putative exon splicing regulatory element that we aimed to block in order to induce the elimination of that exon during the splicing process. All experiments were performed according to protocols as described for the skipping of exon 46 (see above). Gel mobility shift assays were performed to identify those hAONs with high binding affinity for the target RNA. We selected the five hAONs that showed the highest affinity. These hAONs were transfected into human control muscle cell cultures in order to test the feasibility of skipping exon 51 in vitro. RNA was isolated 24 hours post-transfection, and cDNA was generated using an exon 53- or 65-specific reverse primer. PCR-amplification of the targeted region was performed using different primer combinations flanking exon 51. The RT-PCR and sequence analysis revealed that we were able to induce the specific skipping of exon 51 from the human dystrophin transcript. We subsequently transfected two hAONs (#23 and #29) shown to be capable of inducing skipping of the exon into six different muscle cell cultures derived from DMD-patients carrying one of the mutations mentioned above. The skipping of exon 51 in these cultures was confirmed by RT-PCR and sequence analysis (FIG. 7). More importantly, immunohistochemical analysis, using multiple antibodies raised against different parts of the dystrophin protein, showed in all cases that, due to the skipping of exon 51, the synthesis of a dystrophin protein was restored.

Exon 51-specific hAONs:

hAON#21: 5' CCACAGGTTGTGTCACCAG     (SEQ ID NO: 16)

hAON#22: 5' TTTCCTTAGTAACCACAGGTT  (SEQ ID NO: 17)

hAON#23: 5' TGGCATTTCTAGTTTGG      (SEQ ID NO: 18)

hAON#24: 5' CCAGAGCAGGTACCTCCAACATC (SEQ ID NO: 19)

hAON#25: 5' GGTAAGTTCTGTCCAAGCCC   (SEQ ID NO: 20)

hAON#26: 5' TCACCCTCTGTGATTTTAT    (SEQ ID NO: 21)

hAON#27: 5' CCCTCTGTGATTTT         (SEQ ID NO: 22)

hAON#28: 5' TCACCCACCATCACCCT      (SEQ ID NO: 23)

hAON#29: 5' TGATATCCTCAAGGTCACCC   (SEQ ID NO: 24)

hAON#30: 5' CTGCTTGATGATCATCTCGTT  (SEQ ID NO: 25)

Simultaneous Skipping of Multiple Dystrophin Exons

The skipping of one additional exon, such as exon 46 or exon 51, restores the reading frame for a considerable number of different DMD mutations. The range of mutations for which this strategy is applicable can be enlarged by the simultaneous skipping of more than one exon. For instance, in DMD patients with a deletion of exon 46 to exon 50, only the skipping of both the deletion-flanking exons 45 and 51 enables the reestablishment of the translational reading frame.

ERS-Independent Exon Skipping

Figure 8A:
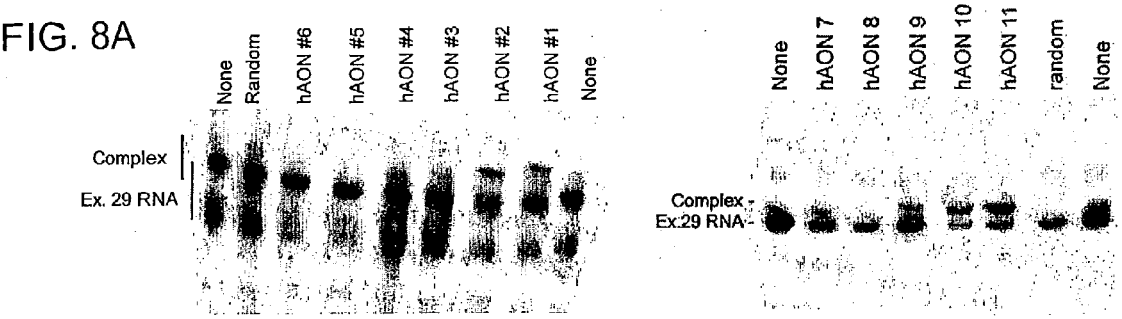
FIG. 8A. Gel mobility shift assays were performed to determine the binding affinity of the different h29AON#'s for the exon 29 target RNA. When compared to non-hybridized RNA (none), h29AON#1, #2, #4, #6, #9, #10, and #11 generated complexes with lower gel mobilities, indicating their binding to the RNA. A random AON derived from dystrophin exon 19 did not generate a complex.
Figure 8B:
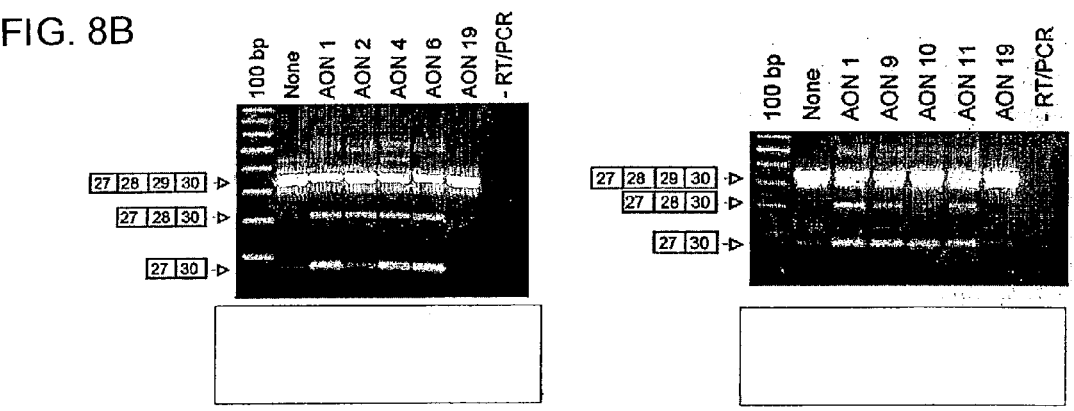
FIG. 8B. RT-PCR analysis of RNA isolated from human control muscle cell cultures treated with h29AON#1, #2, #4, #6, #9, #10, or #11 revealed a truncated product of which the size corresponded to exon 28 spliced to exon 30. These results indicate that exon 29 can specifically be skipped using AONs directed to sequences either within (h29AON#1, #2, #4, or #6) or outside (h29AON#9, #10, or #11) the hypothesized ERS in exon 29. An additional aberrant splicing product was observed that resulted from skipping of both exon 28 and exon 29 (confirmed by sequence data not shown). Although this product was also present in non-treated cells, suggesting that this alternative skipping event may occur naturally, it was enhanced by the AON-treatment. AON 19, derived from dystrophin exon 19, did not induce exon 29 skipping.
Figure 8C:
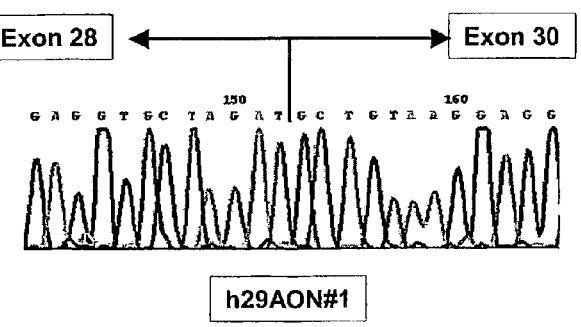
FIG. 8C. The specific skipping of exon 29 was confirmed by sequence data from the truncated RT-PCR fragments. Shown here is the sequence obtained from the exon 29 skipping product in cells treated with h29AON#1.

A mutation in exon 29 leads to the skipping of this exon in two Becker muscular dystrophy patients (Ginjaar at al., 2000, EJHG, vol. 8, p. 793-796). We studied the feasibility of directing the skipping of exon 29 through targeting the site of mutation by AONs. The mutation is located in a purine-rich stretch that could be associated with ERS activity. We designed a series of AONs (see below) directed to sequences both within (h29AON#1 to h29AON#6) and outside (h29AON#7 to h29AON#11) the hypothesized ERS. Gel mobility shift assays were performed (as described) to identify those AONs with highest affinity for the target RNA (FIG. 8). Subsequently, h29AON#1, #2, #4, #6, #9, #10, and #11 were transfected into human control myotube cultures using the PEI transfection reagent. RNA was isolated 24 hrs post-transfection, and cDNA was generated using an exon 31-specific reverse primer. PCR-amplification of the targeted region was performed using different primer combinations flanking exon 29. This RT-PCR and subsequent sequence analysis (FIGS. 8B and 8C) revealed that we were able to induce the skipping of exon 29 from the human dystrophin transcript. However, the AONs that facilitated this skipping were directed to sequences both within and outside the hypothesized ERS (h29AON#1, #2, #4, #6, #9, and #11). These results suggest that skipping of exon 29 occurs independent of whether or not exon 29 contains an ERS and that, therefore, the binding of the AONs to exon 29 more likely inactivated an exon inclusion signal rather than an ERS. This proof of ERS-independent exon skipping may extend the overall applicability of this therapy to exons without ERS's.

```
h29AON#1:
5' TATCCTCTGAATGTCGCATC      (SEQ ID NO: 26)

h29AON#2:
5' GGTTATCCTCTGAATGTCGC      (SEQ ID NO: 27)

h29AON#3:
5' TCTGTTAGGGTCTGTGCC        (SEQ ID NO: 28)

h29AON#4:
5' CCATCTGTTAGGGTCTGTG       (SEQ ID NO: 29)

h29AON#5:
5' GTCTGTGCCAATATGCG         (SEQ ID NO: 30)

h29AON#6:
5' TCTGTGCCAATATGCGAATC      (SEQ ID NO: 31)

h29AON#7:
5' TGTCTCAAGTTCCTC           (SEQ ID NO: 32)

h29AON#8:
5' GAATTAAATGTCTCAAGTTC      (SEQ ID NO: 33)

h29AON#9:
5' TTAAATGTCTCAAGTTCC        (SEQ ID NO: 34)

h29AON#10:
5' GTAGTTCCCTCCAACG          (SEQ ID NO: 35)

h29AON#11:
5' CATGTAGTTCCCTCC           (SEQ ID NO: 36)
```

AON-Induced Exon 46 Skipping In Vivo in Murine Muscle Tissue.

Figure 9A:
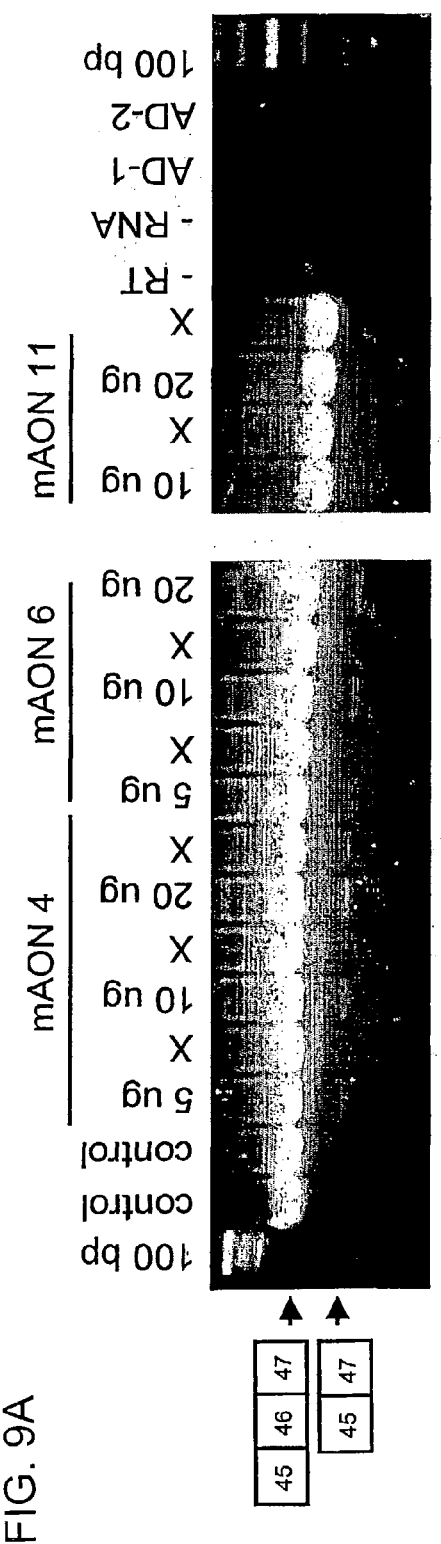
FIG. 9A. RT-PCR analysis of RNA isolated from mouse gastrocnemius muscles two days post-injection of 5, 10, or 20 μg of either mAON#4, #6, or #11. Truncated products, with a size corresponding to exon 45 spliced to exon 47, were detected in all treated muscles. The samples -RT, -RNA, AD-1, and AD-2 were analyzed as negative controls for the RT-PCR reactions.
Figure 9B:
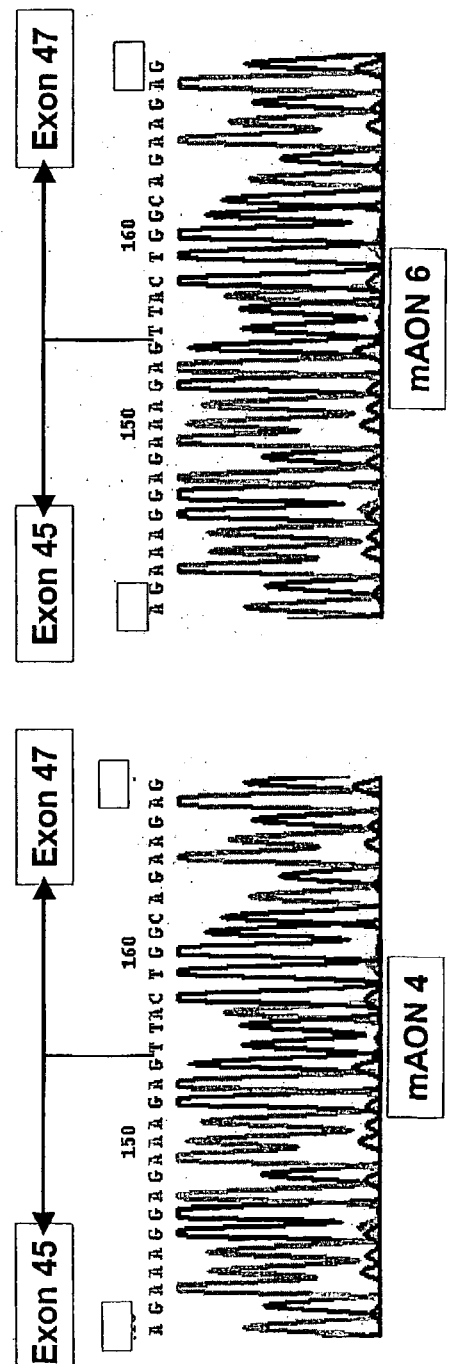
FIG. 9B. Sequence analysis of the truncated products generated by mAON#4 and #6 (and #11, not shown) confirmed the precise skipping of exon 46.

Following the promising results in cultured muscle cells, we tested the different mouse dystrophin exon 46-specific AONs in vivo by injecting them, linked to polyethylenimine (PEI), into the gastrocnemius muscles of control mice. With mAON#4, #6, and #11, previously shown to be effective in mouse muscle cells in vitro, we were able to induce the skipping of exon 46 in muscle tissue in vivo as determined by both RT-PCR and sequence analysis (FIG. 9). The in vivo exon 46 skipping was dose-dependent with highest efficiencies (up to 10%) following injection of 20 μg per muscle per day for two subsequent days.

REFERENCES

Achsel et al., 1996, J. Biochem. 120, pp. 53-60.
Bruice T. W. and Lima, W. F., 1997, Biochemistry 36(16): pp. 5004-5019.
Brunak at al., 1991, J. Mol. Biol. 220, pp. 49-65.
Dunckley, M. G. et al., 1998, Human molecular genetics 7, pp. 1083-1090.
Ginjaar et al., 2000, EJHG, vol. 8, pp. 793-796.
Mann et al., 2001, PNAS vol. 98, pp. 42-47.
Tanaka et al., 1994 Mol. Cell. Biol. 14, pp. 1347-1354.
Wilton, S. D., et al., 1999, Neuromuscular disorders 9, pp. 330-338.
Details and background on Duchenne Muscular Dystrophy and related diseases can be found on website worldwideweb.dmd.nl

What is claimed is:

1. A method for directing splicing of a dystrophin pre-mRNA in a first cell, the method comprising:

contacting said dystrophin pre-mRNA in said first cell with a first antisense oligonucleotide having from 14 to 40 nucleotides, and being complementary to a portion of a first exon of the dystrophin pre-mRNA, said first exon selected from the group consisting of exon number 2, 8, 29, 43, 44, 45, 46, 50, 51, 52 and 53 of a dystrophin gene, and wherein said first antisense oligonucleotide is able to bind to said first exon and mask said first exon from said first cell's splicing apparatus, providing said first cell with a second antisense oligonucleotide, said second antisense oligonucleotide having from 14 to 40 nucleotides, and being complementary to a portion of a second exon of said dystrophin pre-mRNA wherein said second exon is different from said first exon, wherein said second antisense oligonucleotide is able to bind to said second exon and mask the second exon from the first cell's splicing apparatus, splicing said dystrophin pre-mRNA, and translating an mRNA produced from splicing of said dystrophin pre-mRNA to form a final mRNA excluding said first exon and said second exon, wherein said translation of said mRNA results in a mutant dystrophin protein having a Becker mutant's functionality, wherein said first antisense oligonucleotide is obtained by:
providing a second cell with said first oligonucleotide, the cell having a pre-mRNA containing said first exon, culturing said second cell to form mRNA in said second cell from said pre-mRNA in said second cell, and determining whether said first exon is absent from the thus formed mRNA in said second cell, wherein said second antisense oligonucleotide is obtained by:

providing a third cell or said second cell with said second oligonucleotide, said third cell or said second cell having a pre-mRNA containing said second exon, culturing said third cell or said second cell to form mRNA in said third cell or said second cell from said pre-mRNA in said third cell or said second cell, and determining whether said second exon is absent from the thus formed mRNA in said third cell or said second cell, and wherein the method of determining whether said first exon or said second exon is absent from the thus formed mRNA comprises RT-PCR and sequence analysis.

2. The method according to claim 1, wherein said first and/or second antisense oligonucleotide is a 2'O-methyl phosphorothioate oligoribonucleotide or a peptide nucleic acid.

3. The method according to claim 1, wherein said first exon is exon 45 of dystrophin and wherein said second exon is exon 51 of dystrophin.

4. The method according to claim 1, wherein said first and/or said second antisense oligonucleotide have from 14 to 25 nucleotides.

* * * * *